United States Patent [19]
Wahlstrand et al.

[11] Patent Number: 5,271,395
[45] Date of Patent: Dec. 21, 1993

[54] METHOD AND APPARATUS FOR RATE-RESPONSIVE CARDIAC PACING

[75] Inventors: John D. Wahlstrand, Shoreview; Girard B. Borgerding, Minneapolis; Daniel R. Greeninger, Coon Rapids; Daniel J. Baxter, St. Paul, all of Minn.

[73] Assignee: Medtronic, Inc., Minneapolis, Minn.

[21] Appl. No.: 870,062

[22] Filed: Apr. 17, 1992

[51] Int. Cl.$^5$ .............................................. A61N 1/362
[52] U.S. Cl. ........................................... 607/9; 128/734
[58] Field of Search ........................ 128/419 PG, 734

[56] References Cited

U.S. PATENT DOCUMENTS

| | | | |
|---|---|---|---|
| 4,257,423 | 3/1981 | McDonald et al. | 128/419 |
| 4,305,397 | 12/1981 | Weisbrod et al. | 128/419 |
| 4,323,074 | 4/1982 | Nelms | 128/419 |
| 4,379,459 | 4/1983 | Stein | 128/419 |
| 4,476,868 | 10/1984 | Thompson | 128/419 |
| 4,485,813 | 12/1984 | Anderson et al. | 128/675 |
| 4,550,370 | 10/1985 | Baker | 364/413 |
| 4,556,063 | 12/1985 | Thompson et al. | 128/419 |
| 4,702,253 | 10/1987 | Nappholz et al. | 128/419 |
| 4,919,136 | 4/1990 | Alt | 128/419 P |
| 5,063,927 | 11/1991 | Webb et al. | 128/419 |
| 5,127,404 | 7/1992 | Wyborny et al. | 128/419 |

Primary Examiner—William E. Kamm
Assistant Examiner—Kennedy J. Schaetzle
Attorney, Agent, or Firm—Dwight N. Holmbo; Harold R. Patton

[57] ABSTRACT

A rate-responsive cardiac pacemaker comprising a minute ventilation circuit and an activity circuit. The minute ventilation circuit computes a first target pacing rate as a function of measurements of the patient's pleural blood impedance, and the activity circuit computes a second target pacing rate as a function of measured levels of patient activity. A rate control function establishes a rate-responsive pacing rate based on the first and second target pacing rates. The minute ventilation circuit delta-modulates an analog impedance waveform and maintains short-term and long-term weighted averages of delta-modulator output counts. Variations in the difference between the short-term and long-term weighted average values are determinative of the first target pacing rate. Variations in an activity sensor output signal are determinative of the second target pacing rate. Physician-programmable parameters for the pacemaker include selection of a rate-response setting, upper and lower pacing rate limits, and rate-smoothing attack and decay settings.

9 Claims, 9 Drawing Sheets

METHOD AND APPARATUS FOR RATE-RESPONSIVE CARDIAC PACING

FIELD OF THE INVENTION

This invention relates generally to the field of cardiac pacemakers, and more particularly relates to cardiac pacemakers of the type which measure the metabolic demand for oxygenated blood and vary the pacing rate of the pacemaker in accordance therewith.

BACKGROUND OF THE INVENTION

A wide variety of cardiac pacemakers are known and commercially available. Pacemakers are generally characterized by which chambers of the heart they are capable of sensing, the chambers to which they deliver pacing stimuli, and their responses, if any, to sensed intrinsic electrical cardiac activity. Some pacemakers delivery pacing stimuli at fixed, regular intervals without regard to naturally occurring cardiac activity. More commonly, however, pacemakers sense electrical cardiac activity in one or both of the chambers of the heart, and inhibit or trigger delivery of pacing stimuli to the heart based on the occurrence and recognition of sensed intrinsic electrical events. A so-called "VVI" pacemaker, for example, senses electrical cardiac activity in the ventricle of the patient's heart, and delivers pacing stimuli to the ventricle only in the absence of electrical signals indicative of natural ventricular contractions. A "DDD" pacemaker, on the other hand, senses electrical signals in both the atrium and ventricle of the patient's heart, and delivers atrial pacing stimuli in the absence of signals indicative of natural atrial contractions, and ventricular pacing stimuli in the absence of signals indicative of natural ventricular contractions. The delivery of each pacing stimulus by a DDD pacemaker is synchronized with prior sensed or paced events.

Pacemakers are also known which respond to other types of physiologically-based signals, such as signals from sensors for measuring the pressure inside the patient's ventricle or for measuring the level of the patient's physical activity. In recent years, pacemakers which measure the metabolic demand for oxygen and vary the pacing rate in response thereto have become widely available. Perhaps the most popularly employed method for measuring the need for oxygenated blood is to measure the physical activity of the patient by means of a piezoelectric transducer. Such a pacemaker is disclosed in U.S. Pat. No. 4,485,813 issued to Anderson et al.

In typical prior art rate-responsive pacemakers, the pacing rate is determined according to the output from an activity sensor. The pacing rate is variable between a predetermined maximum and minimum level, which may be selectable by a physical from among a plurality of programmable upper and lower rate limit settings. When the activity sensor output indicates that the patient's activity level has increased, the pacing rate is increased from the programmed lower rate by an incremental amount which is determined as a function of the output of the activity sensor. That is, the rate-responsive or "target" pacing rate in a rate-responsive pacemaker is determined as follows:

Target Rate = Programmed Lower Rate + $f$(sensor output)

where $f$ is typically a linear or monotonic function of the sensor output. As long as patient activity continues to be indicated, the pacing rate is periodically increased by incremental amounts calculated according to the above formula, until the programmed upper rate limit is reached. When patient activity ceases, the pacing rate is gradually reduced, until the programmed lower rate limit is reached.

In an effort to minimize patient problems and to prolong or extend the useful life of an implanted pacemaker, it has become common practice to provide numerous programmable parameters in order to permit the physical to select and/or periodically adjust the desired parameters or to match or optimize the pacing system to the patient's physiologic requirements. The physician may adjust the output energy settings to maximize pacemaker battery longevity while ensuring an adequate patient safety margin. Additionally, the physician may adjust the sensing threshold to ensure adequate sensing of intrinsic depolarization of cardiac tissue, while preventing oversensing of unwanted events such as myopotential interference or electromagnetic interference (EMI). Also, programmable parameters are typically required to enable and to optimize a pacemaker rate response function. For example, Medtronic, Inc.'s Legend and Activitrax series of pacemakers are multiprogrammable, rate-responsive pacemakers having the following programmable parameters: pacing mode, sensitivity, refractory period, pulse amplitude, pulse width, lower and upper rate limits, rate response gain, and activity threshold.

For any of the known rate-responsive pacemakers, it is clearly desirable that the sensor output correlate to as high a degree as possible with the actual metabolic and physiologic needs of the patient, so that the resulting rate-responsive pacing rate may be adjusted to appropriate levels. A piezoelectric activity sensor can only be used to indirectly determine the metabolic need. The physical activity sensed can be influenced by upper body motion. Therefore, an exercise that involves arm motion may provide signals that are inappropriately greater than the metabolic need. Conversely, exercises that stimulate the lower body only, such as bicycle riding, may provide a low indication of metabolic need while the actual requirement is very high. Therefore, it would be desirable to implement a rate-responsive pacemaker that is based on a parameter that is correlated directly to metabolic need.

Minute ventilation ($V_6$) has been demonstrated clinically to be a parameter that correlates directly to the actual metabolic and physiologic needs of the patient. Minute ventilation is defined by the equation:

$$V_c = RR \times VT$$

where RR = respiration rate in breaths per minute (bpm), and VT = tidal volume in liters. Clinically, the measurement of $V_c$ is performed by having the patient breathe directly into a device that measurements the exchange of air and computes the total volume per minute. The direct measurement of $V_c$ is not possible with an implanted device. However, measurement of the impedance changes of the thoracic cavity can be implemented with an implanted pacemaker. Such a pacemaker is disclosed in U.S. Pat. No. 4,702,253 issued to Nappholz et al. on Oct. 27, 1987. The magnitude of the change of the impedance signal corresponds to the tidal volume and the frequency of change corresponds to respiration rate.

The use of transthoracic impedance to indicate $V_c$ has a significant spurious false positive due to upper body myopotential interference and postural changes. Further, slow-acting physiologic parameters such as transitory blood chemistry changes also impact the impedance amplitude. Therefore, it may be desirable to define a rate response function f which minimizes the effects of spurious or transitory changes in impedance sensor output which do not accurately indicate the patient's metabolic needs.

Additionally, basing the pacing rate solely on $V_c$ does not provide the optimum pacing rate increase at the onset of exercise. The VT and RR have an inherent physiologic time delay due to the response of the $CO_2$ receptors and the autonomic nervous system. The increase in $V_c$ lags behind the need for the increased cardiac output. Therefore, it may also be desirable to implement a rate response function f that is based on a combination of a fast responding sensor such as an activity sensor and a physiologically delayed metabolic sensor such as $V_c$.

The combination of the activity and $V_c$ sensor outputs for a rate response function in a manner where the faster of the two independently derived target pacing rates would be utilized as the actual pacing rate is believed to be effective. Such an 'OR' combination of sensor signals is disclosed, for example, in U.S. Pat. No. 5,063,927 issued to Webb et al., which patent is incorporated herein by reference. Combining an activity-based target rate and a metabolic-based target rate in the manner suggested by Webb et al. would provide the fast onset of an activity sensor with the sustained response of a $V_c$ sensor. Provisions in the rate response function f would need to include lower and upper rate limits, along with a mapping function from impedance to pacing rate that could be adjusted by a physician to optimize the function for each patient.

SUMMARY OF THE INVENTION

In one disclosed embodiment of the invention, a pacemaker having an impedance-based minute ventilation sensor and an acoustical energy, pressure, or other type of activity sensor computes a target rate-responsive pacing rate based upon a function of the two sensors' outputs.

In the disclosed embodiment of the invention, processing of the impedance-based minute ventilation sensor occurs independently of the processing of other activity sensor signals, and two or more "target" rate-responsive pacing rates are independently determined. Further computation results in a rate-responsive pacing rate which represents some function of the independently determined target rates.

In one disclosed embodiment of the invention, the minute ventilation is determined using the change of impedance of the tripolar transthoracic impedance vector. A current is forced between the pacemaker's conductive housing and the ring electrode of the pacemakers transvenous lead, and the resultant voltage is measured at the tip electrode of the lead with reference to the case. The DC component of the impedance signal is removed and the AC component processed by a delta-modulator function. The delta-modulator resolves the change in the analog impedance signal voltage into digital counts or pulses, the number of counts being proportional to the change. The counts are summed over an interval of two seconds to produce the product of amplitude and rate. The impedance-based target pacing period is then determined as a function of this minute ventilation signal.

In another embodiment of the invention, impedance is determined from the intracardiac vector measured from the ring electrode to the tip electrode of the pacemaker lead. The signal is processed with LP filtering to remove the cardiac component. The target pacing rate may then be determined using the processed impedance signal.

BRIEF DESCRIPTION OF THE DRAWINGS

The foregoing and other features of the present invention will be best appreciated with reference to the detailed description of a specific embodiment of the invention, which follows, when read in conjunction with accompanying drawings, wherein.

DETAILED DESCRIPTION OF A SPECIFIC EMBODIMENT OF THE INVENTION

Figure 1:
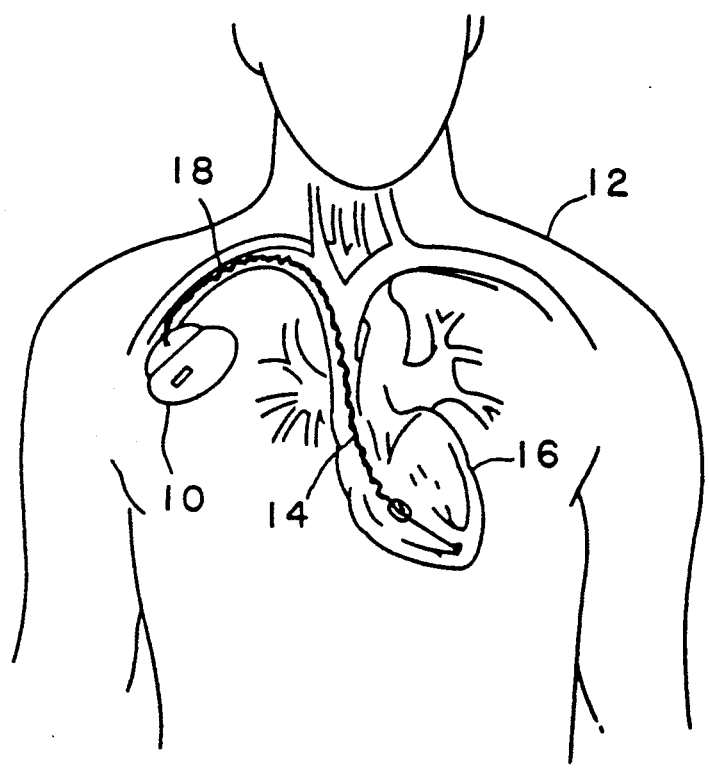
FIG. 1 is a diagram showing the placement in the patient of a pacemaker in accordance with one embodiment of the present invention.

FIG. 1 shows generally where a pacemaker 10 in accordance with one embodiment of the present invention may be implanted in a patient 12. It is to be understood that pacemaker 10 is contained within a hermetically-sealed, biologically inert outer shield or "can", in accordance with common practice in the art. A pacemaker lead 14 is electrically coupled to pacemaker 10 and extends into the patient's heart 16 via a vein 18. The distal end of lead 14 includes one or more exposed conductive electrodes for receiving electrical cardiac signals and/or for delivering electrical pacing stimuli to the heart 16. Lead 14 may be implanted with its distal end situated in the atrium or ventricle of heart 16.

Figure 2:
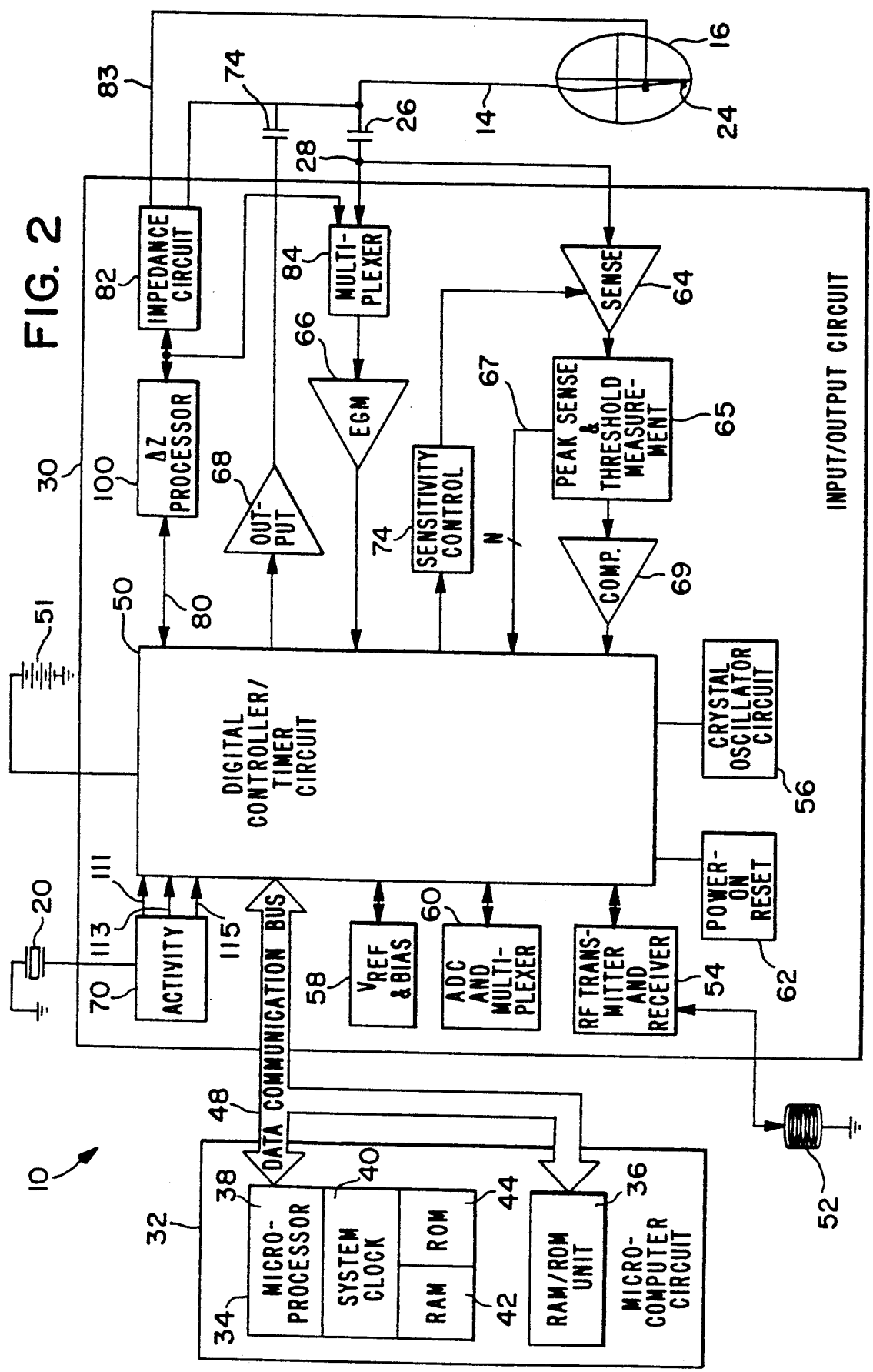
FIG. 2 is a block diagram of functional components of the pacemaker of FIG. 1.

Turning now to FIG. 2, a block diagram of pacemaker 10 from FIG. 1 is shown. Although the present invention will be described herein in conjunction with a pacemaker 10 having a microprocessor-based architecture, it will be understood that pacemaker 10 may be implemented in any logic based, custom integrated circuit architecture, if desired. It will also be understood that the present invention may be utilized in conjunction with other implantable medical devices, such as cardioverters, defibrillators, cardiac assist systems, and the like.

In the illustrative embodiment shown in FIG. 2, pacemaker 10 includes an activity sensor 20, which may be, for example, a piezoelectric element bonded to the inside of the pacemaker's shield. Such a pacemaker/activity sensor configuration is the subject of the above-referenced patent to Anderson et al., which is hereby incorporated by reference in its entirety. Piezoelectric sensor 20 provides a sensor output which varies as a function of a measured parameter that relates to the metabolic requirements of patient 12.

Pacemaker 10 of FIG. 2 is programmable by means of an external programming unit (not shown in the Figures). One such programmer suitable for the purposes of the present invention is the Medtronic Model 9760 programmer which has been commercially available for several years and is intended to be used with all Medtronic pacemakers. The programmer is a microprocessor device which provides a series of encoded signals to pacemaker 10 by means of a programming head which transmits radio-frequency (RF) encoded signals to pacemaker 10 according to the telemetry system laid out, for example, in U.S. Pat. No. 4,305,397 issued to Weisbrod et al. on Dec. 15, 1981, U.S. Pat. No. 4,323,074 issued to Nelms on Apr. 6, 1982, or in U.S. Pat. No. 4,550,370 issued to Baker on Oct. 29, 1985, all of which are hereby incorporated by reference in their entirety. It is to be understood, however, that the programming methodologies disclosed in the above-referenced patents are identified herein for the purposes of illustration only, and that any programming methodology may be employed so long as the desired information is transmitted to the pacemaker. It is believed that one of skill in the art would be able to choose from any of a number of available programming techniques to accomplish this task.

The programmer facilitates the selection by a physician of the desired parameter to be programmed and the entry of a particular setting for the desired parameter. For purposes of the present invention, the specifics of operation of the programmer are not believed to be important with the exception that whatever programmer is used must include means for selecting an upper rate (UR), a lower rate (LR), and one of a plurality of rate response (RR) settings to be hereinafter described in greater detail.

In the illustrative embodiment, the lower rate may be programmable, for example from 40 to 90 pulses per minute (PPM) in increments of 10 PPM, the upper rate may be programmable between 100 and 170 PPM in 10 PPM increments, and there may be 16 rate response functions, numbered one through sixteen, available.

In addition, the programmer may include means for selection of acceleration and deceleration parameters which limit the rate of change of the pacing rate. Typically, these parameters are referred to in rate responsive pacemakers as acceleration and deceleration settings, respectively, or attack and decay settings, respectively. These may be expressed in terms of the time interval required for the pacemaker to change between the current pacing rate and 90% of the desired pacing interval, assuming that the activity level corresponding to the desired pacing rate remains constant. Appropriate selectable values for the acceleration time would be, for example, 0.25 minutes, 0.5 minutes, and 1 minute. Appropriate selectable values for the deceleration time would be, for example, 2.5 minutes, 5 minutes, and 10 minutes.

Pacemaker 10 is schematically shown in FIG. 2 to be electrically coupled via a pacing lead 14 to a patient's heart 16. Lead 14 includes an intracardiac tip electrode 24 located near its distal end and positioned within the right ventricular (RV) or right atrial (RA) chamber of heart 16. Lead 14 is a bipolar electrode, as is well known in the art. Although an application of the present invention in the context of a single-chamber pacemaker will be disclosed herein for illustrative purposes, it is to be understood that the present invention is equally applicable in dual-chamber pacemakers.

Electrode 24 is coupled via suitable lead conduit 14 through input capacitor 26 to node 28 and to input/output terminals of an input/output circuit 30. In the presently disclosed embodiment, activity sensor 20 is bonded to the inside of the pacemaker's outer protective shield, in accordance with common practice in the art. As shown in FIG. 2, the output from activity sensor 20 is coupled to input/output circuit 30.

Input/output circuit 30 contains the analog circuits for interface to the heart 16, activity sensor 20, antenna 52, as well as circuits for the application of stimulating pulses to heart 16 to control its rate as a function thereof under control of the software-implemented algorithms in a microcomputer circuit 32.

Microcomputer circuit 32 comprises an on-board circuit 34 and an off-board circuit 36. On-board circuit 34 includes a microprocessor 38, a system clock circuit 40, and on-board RAM 42 and ROM 44. In the presently disclosed embodiment of the invention, off-board circuit 36 includes a RAM/ROM unit. On-board circuit 34 and off-board circuit 36 are each coupled by a data communication bus 48 to a digital controller/timer circuit 50. Microcomputer circuit 32 may be fabricated of a custom integrated circuit device augmented by standard RAM/ROM components.

It will be understood that the electrical components represented in FIG. 1 are powered by an appropriate implantable battery power source 51, in accordance with common practice in the art. For the sake of clarity, the coupling of battery power to the various components of pacemaker 10 has not been shown in the Figures.

An antenna 52 is connected to input/output circuit 30 for purposes of uplink/downlink telemetry through RF transmitter and receiver unit 54. Unit 54 may correspond to the telemetry and program logic employed in U.S. Pat. No. 4,566,063 issued to Thompson et al. on Dec. 3, 1985 and U.S. Pat. No. 4,257,423 issued to McDonald et al. on Mar. 24, 1981, both of which are incorporated herein by references in their entirety. Telemetering analog and/or digital data between antenna 52 and an external device, such as the aforementioned external programmer (not shown), may be accomplished in the presently disclosed embodiment by means of all data first being digitally encoded and then pulse-position modulated on a damped RF carrier, as substantially described in co-pending U.S. patent application Ser. No. 468,407, filed on Jan. 22, 1990, entitled "Improved Telemetry Format", which is assigned to the assignee of the present invention and which is incorporated herein by reference. The particular programming and telemetry scheme chosen is not believed to be important for the purposes of the present invention so long as it provides for entry and storage of values of rate-response parameters discussed herein.

A crystal oscillator circuit 56, typically a 32,768-Hz crystal-controlled oscillator, provides main timing clock signals to digital controller/timer circuit 50. A $V_{REF}$ and Bias circuit 58 generates stable voltage reference and bias currents for the analog circuits of input-/output circuit 30. An analog-to-digital converter (ADC) and multiplexer unit 60 digitizes analog signals and voltage to provide "real-time" telemetry intracardiac signals and battery end-of-life (EOL) replacement function. A $\Delta Z$ Processor 100 is utilized in conjunction with output signals from impedance sensors, as shall be hereinafter described in greater detail. A power-on-reset (POR) circuit 62 functions as a means to reset circuitry and related functions to a default condition upon detection of a low battery condition, which will occur upon initial device power-up or will transiently occur in the presence of electromagnetic interference, for example.

The operating commands for controlling the timing of pacemaker 10 are coupled by bus 48 to digital controller/timer circuit 50 wherein digital timers and counters are employed to establish the overall escape interval of the pacemaker, as well as various refractory, blanking, and other timing windows for controlling the operation of the peripheral components within input-/output circuit 30.

Digital controller/timer circuit 50 is coupled to sensing circuitry including a sense amplifier 64, a peak sense and threshold measurement unit 65, and a comparator/threshold detector 69. Circuit 50 is further coupled to receive an output signal from an electrogram (EGM) amplifier 66. EGM amplifier 66 receives, amplifies and processes electrical signals provided from multiplexor 84. Multiplexor 84 receives a signal from 1 of 2 places: 1) electrode 24, lead conductor 14 and capacitor 26, this signal being representative of the electrical activity of the patient's heart 16; and 2) an impedance waveform resulting from operation of an impedance circuit 82 (to be hereinafter described in detail).

A sense amplifier 64 amplifies sensed electrical cardiac signals and provides this amplified signal to peak sense and threshold measurement circuitry 65, which provides an indication of peak sensed voltages and the measured sense amplifier threshold voltage on multiple conductor signal path 67 to digital controller/timer circuit 50. The amplifier sense amplifier signal is then provided to comparator/threshold detector 69. Sense amplifier 64 may correspond, for example, to that disclosed in U.S. Pat. No. 4,379,459 issued to Stein on Apr. 12, 1983, incorporated by reference herein in its entirety. The electrogram signal developed by EGM amplifier 66 is used on those occasions when the implanted device is being interrogated by an external programmer, not shown, to transmit by uplink telemetry a representation of the analog electrogram of the patient's electrical heart activity, such as described in U.S. Pat. No. 4,556,063, issued to Thompson et al., assigned to the assignee of the present invention and incorporated herein by reference. As previously noted, EGM amplifier 66 also selectively receives an impedance waveform which may also be transmitted by uplink telemetry to an external programmer.

An output pulse generator 68 provides pacing stimuli to the patient's heart 16 through coupling capacitor 74 in response to a pacing trigger signal developed by digital controller/timer circuit 50 each time the escape interval times out, or an externally transmitted placing command has been received, or in response to other stored commands as is well known in the pacing art. Output amplifier 68 may correspond generally to the output amplifier disclosed in U.S. Pat. No. 4,476,868 issued to Thompson on Oct. 16, 1984 also incorporated herein by reference in its entirety.

While specific embodiments of input amplifier 64, output amplifier 68, and EGM amplifier 66 have been identified herein, this is done for the purposes of illustration only. It is believed by the inventor that the specific embodiments of such circuits are not critical to the present invention so long as they provide means for generating a stimulating pulse and provide digital controller/timer circuit 50 with signals indicative of natural and/or stimulated contractions of the heart.

Digital controller/timer circuit 50 is coupled to an activity circuit 70 for receiving, processing, and amplifying signals received from activity sensor 20. Digital controller/timer circuit 50 is also coupled, via line 80 to a ΔZ Processor circuit 100, which in turn is coupled to an impedance circuit 82. Impedance circuit 82 is coupled directly to pacing lead 14. Impedance circuit 82 measures cardiac impedance by outputting periodic biphasic current pulses on pacing lead 14, and then sensing the resulting voltages. The resulting voltages are sensed and demodulated in an AC-coupled manner, to generate a voltage waveform (hereinafter "impedance waveform") which reflects changes in impedance (i.e., with baseline impedance substrated). The utilization of an impedance sensor of this type in a cardiac pacemaker is the subject of the above-reference U.S. Pat. No. 4,702,253 to Nappholz et al., which is hereby incorporated by reference in its entirety. The measured impedance changes will be related to respiratory changes in frequency and magnitude. The analog impedance waveform is scaled and filtered in impedance circuit 82, and the resulting waveform provided to ΔZ Processor 100 for conversion to digital format, as shall be hereinafter described in greater detail.

The time-course of the impedance waveform represents the minute ventilation parameter which will be measured for the purposes of the present disclosure in units of $\Omega x$ (breaths per minute), hereinafter referred to as "Wallys" and symbolized by the Greek letter $\psi$. In accordance with the presently disclosed embodiment of the invention, pacemaker 10 computes two average values which are updated every two seconds. The first average value is the average number of Wallys occurring in each of the sixteeth two-second intervals during the previous thirty-two seconds; this value shall be referred to as the short-term Wally average. The second average value is the average number of Wallys occurring in each of the 1024 two-second intervals during the previous 2048 seconds; this average value shall be referred to as the long-term Wally average. Every two seconds, the relative difference between the long-term Wally average and the short-term Wally average is used to determine the impedance-based target pacing rate. That is, every two seconds, the difference between the long-term Wally average and the short-term Wally average is compared to the value of this difference computed two seconds before. This relative difference value represents the short-term change in respiratory impedance, and has units of $\Omega x$ (breaths, per minute, per second), hereinafter referred to as "Wallys per second" and symbolized by the Greek letter $\Psi$.

Pacemaker 10 in accordance with the presently disclosed embodiment of the invention implements sixteen programmable rate-response settings, which define the resultant impedance-based target pacing rate for a given number of Wallys per second measured. The selectable rate-response settings are numbered 1-16, and are characterized by the number of Wallys per second required to achieve pacing at the programmed upper rate at that setting. In addition to the sixteen rate-response settings, pacemaker 10 is also programmable into one of four possible gain settings. The gain setting determines the factor by which the impedance waveform is scaled prior to analog-to-digital conversion. The following Table 1 sets forth the 16 rate response settings.

TABLE 1

| | Wallys per second - vs - Rate | | | | |
|---|---|---|---|---|---|
| RESPONSE SETTING | GAIN SETTING #1 | GAIN SETTING #2 | GAIN SETTING #3 | GAIN SETTING #4 | RESPONSE INCREASE FROM PREVIOUS SETTING |
| 16 | 1.5 | 3 | 6 | 12 | n/a |
| 15 | 2.25 | 4.5 | 9 | 18 | 50% |
| 14 | 3 | 6 | 12 | 24 | 30% |
| 13 | 3.75 | 7.5 | 15 | 30 | 25% |
| 12 | 5.25 | 10.5 | 21 | 42 | 40% |
| 11 | 6.75 | 13.5 | 27 | 54 | 29% |
| 10 | 8.25 | 16.5 | 33 | 66 | 30% |
| 9 | 9.75 | 19.5 | 39 | 78 | 30% |
| 8 | 11.25 | 22.5 | 45 | 90 | 25% |
| 7 | 13.5 | 27 | 54 | 108 | 30% |
| 6 | 16.5 | 33 | 66 | 132 | 30% |
| 5 | 20.25 | 40.5 | 81 | 162 | 30% |
| 4 | 27.75 | 55.5 | 111 | 222 | 27% |
| 3 | 38.25 | 76.5 | 153 | 306 | 21% |
| 2 | 54 | 108 | 216 | 432 | 23% |
| 1 | 75 | 150 | 300 | 600 | 20% |

As noted above, impedance circuit 82 in accordance with the present invention delivers periodic biphasic current pulses to heart 16; these current pulses are applied to heart 16 via line 83 (which is coupled to lead 14). The resultant voltage waveform is received from lead 14 by impedance circuit 82, which demodulates, filters, and scales the impedance waveform before providing it to $\Delta Z$ Processor 100. In accordance with the presently disclosed embodiment of the invention, $\Delta Z$ Processor 100 is a delta-modulator type data converter. Every 62.5 milliseconds, $\Delta Z$ Processor 100 samples the impedance waveform voltage and outputs a serial bit stream, on line 80, of between 0 and 31 logical '1' bits (where each '2' bit is called a 'count'), the number of counts indicating the magnitude of the change in the impedance waveform voltage since the last sample. That is, the number of counts during each sampling period is proportional to the rate of change of the impedance over time, $dZ/dt$. The magnitude of the change is measured in terms of a number of discrete voltage steps in either the positive or negative direction required to bring the previous reference input of a comparator to the level of the newly sampled voltage input.

The output serial bit stream of $\Delta Z$ Processor 100 shall be hereinafter referred to as DM, which is a value having units of counts per second. The data conversion function of $\Delta Z$ Processor 100 may be then be described as follows:

$$DM = \frac{1}{T} \sum_{t_0}^{t_0+T} dm(i) \quad (i=0,1,2,3,\ldots) \tag{1}$$

where $$dm(i) = dm(t_0+i\Delta t) = \tag{2}$$

$$int\left(\frac{|V_z(t_0+i\Delta t) - V_z(t_0+(i-1)\Delta t)|}{P_{dm}}\right)+1$$

and where $\Delta t = 62.5$ milliseconds  (3)

$P_{dm}$ = precision (i.e., step size) of delta modulator  (4)

and $$int\left(\frac{x}{y}\right) = \text{integer part of } \frac{x}{y} \tag{5}$$

The serial output of $\Delta Z$ Processor 100 on line 80 is processed digitally by digital controller/timer circuit 50 to produce a control variable DZ from which the impedance-based rate-responsive target pacing rate will be calculated. The digital processing of the ADC serial output shall be hereinafter described with reference to FIG. 5. For the purposes of describing the signal processing, several definitions are necessary:

LONG-TERM AVERAGE (LTA)

The LTA value is a parallel output word representing a weighted average of two-second delta modulator counts, with the weighting or emphasis being placed on two-second counts during the latest 2048 seconds. The LTA value is updated every two seconds.

LONG-TERM AVERAGE (LTA) INITIALIZATION PROTOCOL

The LTA initialization protocol is as follows:

The 2048 second Long-Term Average (LTA) value is initialized using an interactive protocol with the programmer. The protocol also determines the correct analog gain range for $\Delta Z$ processing for each patient. The following four ranges are available:

0 to 10 $\Omega$  (first gain range)
0 to 20 $\Omega$  (second gain range)
0 to 20 $\Omega$  (third gain range)
0 to 80 $\Omega$  (fourth gain range)

When the sensor is first enabled, a 32 second countdown is initiated in the pacemaker and the programmer. When the countdown has finished, 32 seconds of delta-modulator counts are loaded into the upper bits of both the Short-Term Average (STA) value and the LTA value. This initializes the difference, DZ (STA−LTA) to zero, (where DZ is the Limited Positive Difference), and the first calculated target rate to a lower rate (LR). Simultaneously, the programmer notifies the user to perform an interrogate which uplinks the value for the LTA. If the LTA is less than or equal to the mid-range value of $\Delta Z$ counts (e.g. 256), then the analog gain remains in the 0 to 10 $\Omega$ range. If the value is greater than mid-range, then the analog gain is increased to the 0 to 20 $\Omega$ and the initialization protocol repeated. If the repeated LTA value is greater than mid-range, then another initialization is repeated in the 0 to 40 $\Omega$ range. This process continues until the LTA is less than or equal to mid-range or the 0 to 80 $\Omega$ range is programmed.

LIMITED SHORT-TERM AVERAGE (LSTA)

The LSTA value is a parallel output word representing the average number of delta-modulator counts occurring in two seconds, over the latest 32 seconds. This value is updated every two seconds. If the rate calculation algorithm in accordance with the presently disclosed embodiment of the invention returns an impedance-based target rate higher than the programmed upper rate limit, the LSTA is not increased further, even if the output of $\Delta Z$ Processor 100 indicates that is should be increased. This prevents saturation of the rate-calculation, and resultant delay in decrease from upper rate when the delta-modulator count is reduced.

LIMITED POSITIVE DIFFERENCE (DZ)

The DZ value represents a comparison between the LSTA and LTA values. The DZ value is a parallel output word which is updated every two seconds according to the following formula:

$$DZ = \begin{cases} 0: & LSTA < LTA \\ LSTA-LTA: & 0 \leq (LSTA-LTA) \leq DZ_{mm} \\ DZ_{mm}: & LSTA-LTA \geq DZ_{mm} \end{cases} \quad (6)$$

The maximum increase in DZ from one two-second value to the next is limited by the UR_DIFF circuitry, as shall be hereinafter described in greater detail.

UNLIMITED SHORT TERM AVERAGE (USTA)

The USTA value is a parallel output word which represents the average number of delta-modulator counts occurring in two seconds, over the latest 32 seconds. USTA is updated every two seconds. Unlike LSTA, however, USTA is not limited by any dependance on the result of the impedance-based rate-response calculation.

UNLIMITED POSITIVE DIFFERENCE FUNCTION (UDZ)

The UDZ value represents a comparison between USTA and LTA, the UDZ value is a parallel output word which is updated every two seconds according to the following formula:

$$UDZ = \begin{cases} 0: & USTA < LTA \\ USTA-LTA: & 0 \leq (USTA-LTA) \leq 127 \\ 127: & USTA-LTA \geq 127 \end{cases} \quad (7)$$

MAXIMUM DZ (MAXDZ)

The MAXDZ value corresponds at all times to the largest UDZ value generated since MAXDZ was last reset.

CLIPPING (UR_DIFF)

The UR_DIFF value is programmable to one of four selectable settings: 1 (nominal value), 2, 4, or 8. The clipping function limits the magnitude of the input signal based on limits that are adjusted based upon the rate-response setting. This function limits the rate change due to false positive signals due to postural or non-respiration muscle motion. The clipping function is disabled when LSTA is less than LTA and during initialization. When enabled, the clipping function limits the input signal to a maximum value computed as follows:

$$\text{INPUT SIGNAL MAXIMUM} = \frac{[DZ_{mm}]}{UR\_DIFF} \quad (8)$$

where $DZ_{mm}$ corresponds to the DZ value resulting in a target pacing period at the programmed upper rate limit (URL).

TARGET PACING PERIOD (TPP)

Each time anew DZ value is computed, the impedance-based TPP can be calculated according to the following formula:

$$TPP = E + \frac{F}{DZ+G} \quad (9)$$

where

| | | | (10) |
|---|---|---|---|
| TPP | = | new target pacing period | |
| E | = | downloadable constant | |
| F | = | downloadable constant | |
| G | = | downloadable constant | |
| DZ | = | latest DZ value | |

Figure 3:
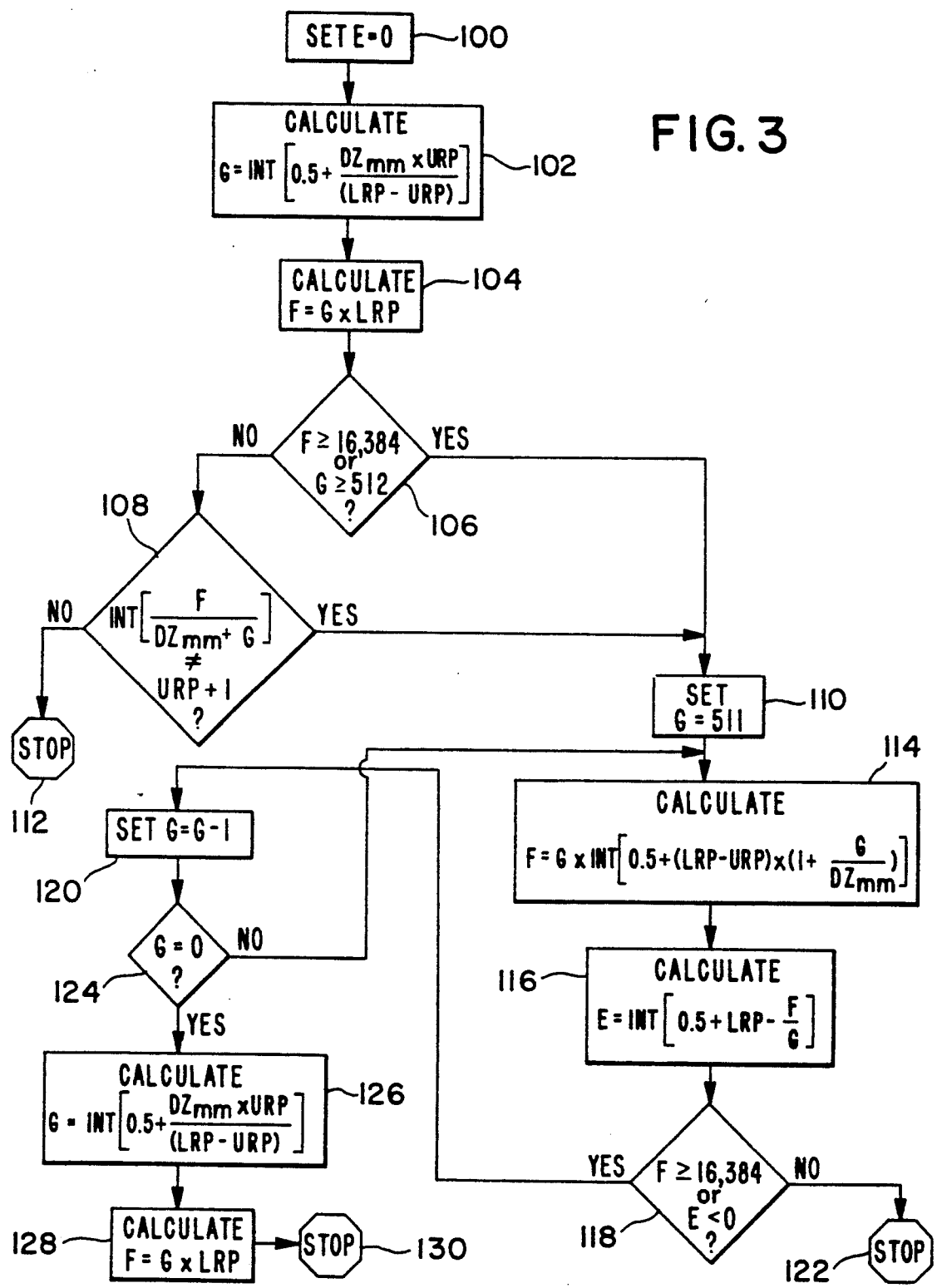
FIG. 3 is a flow diagram illustrating the process for generating certain numerical values used in computations associated with the pacing algorithm of the pacemaker of FIGS. 1 and 2.

The values E, F, and G are chosen based on the currently selected rate response setting (See Table 1 above) and the currently programmed lower rate limit (LRL) and upper rate limit (URL). The process for selecting values for E, F, and G will be best understood with reference to the flow diagram of FIG. 3. In FIG. 3, the process begins at block 100, where the value of E is initialized to zero. Neat, in block 102 the value of G is initialized according to the following formula:

$$G = int\left( 0.5 + \frac{DZ_{mm} \times URP}{LRP - URP} \right) \quad (11)$$

where $DZ_{mm}$ is the minimum DZ value (i.e., the minimum maximum value of DZ) required to reach the programmed upper rate limit at the current rate response setting, LRP is the current lower rate period (expressed in numbers of slow clock cycles per pacing cycle) and URP is the current upper rate period (expressed in numbers of slow clock cycles per pacing cycle). In block 104, F is set to $(G \times LRP)$.

In decision block 106, two comparison are made: if F is greater than or equal to 16,384, or if G is greater than or equal to 512, process flow branches to block 110. If F is not greater than 16,384 and if G is not greater than or equal to 512, process flow branches to block 108.

In block 108, the integer part of the calculation $F/(CZ_{mm}+G)$ is compared with URP+1. If these values are equal, the process stops, as indicated by STOP symbol 112 in FIG. 4. If the two values compared in block 108 are not equal (or, if a "yes" result was reached in decision block 106) process flow proceeds to block 110, where the value of G is set to 511. Then, in block 114, F is calculated according to the following formula:

$$F = G \times int\left\{ 0.5 + (LRP - URP) \times \left( 1 + \frac{G}{DZ_{mm}} \right) \right\} \quad (12)$$

In block 116, E is calculated according to:

$$E = int\left\{ 0.5 + LRP - \frac{F}{G} \right\} \quad (13)$$

Next, in decision block 118, F is compared with the value 16,384 and E is compared with zero. If F is greater than or equal to 16,384 or E is less than zero, process flow branches to block 120; otherwise, process flow stops, as indicated by STOP symbol 122. In block 120, G is decremented by one. In decision block 124, G is compared with zero. If G equals zero, process flow branches to block 126; if G does not equal zero, process flow returns to block 114, and blocks 114, 116, and 118 are repeated. In block 126, G is calculated according to equation 11 described with reference to block 102 above. In block 128, the value $F = G \times LRP$ is computed, and process flow stops, as indicated by STOP symbol 130.

The resultant mapping of DZ values to target pacing rates achieved through the computations described by equations (1) through (13) above may be best appreciated with reference to FIGS. 4a through 4d, which are graphs showing the impedance-based target pacing period (TPP) verses DZ value for all sixteen rate response settings, for six combinations of programmed URL and LRL.

Figure 4A:
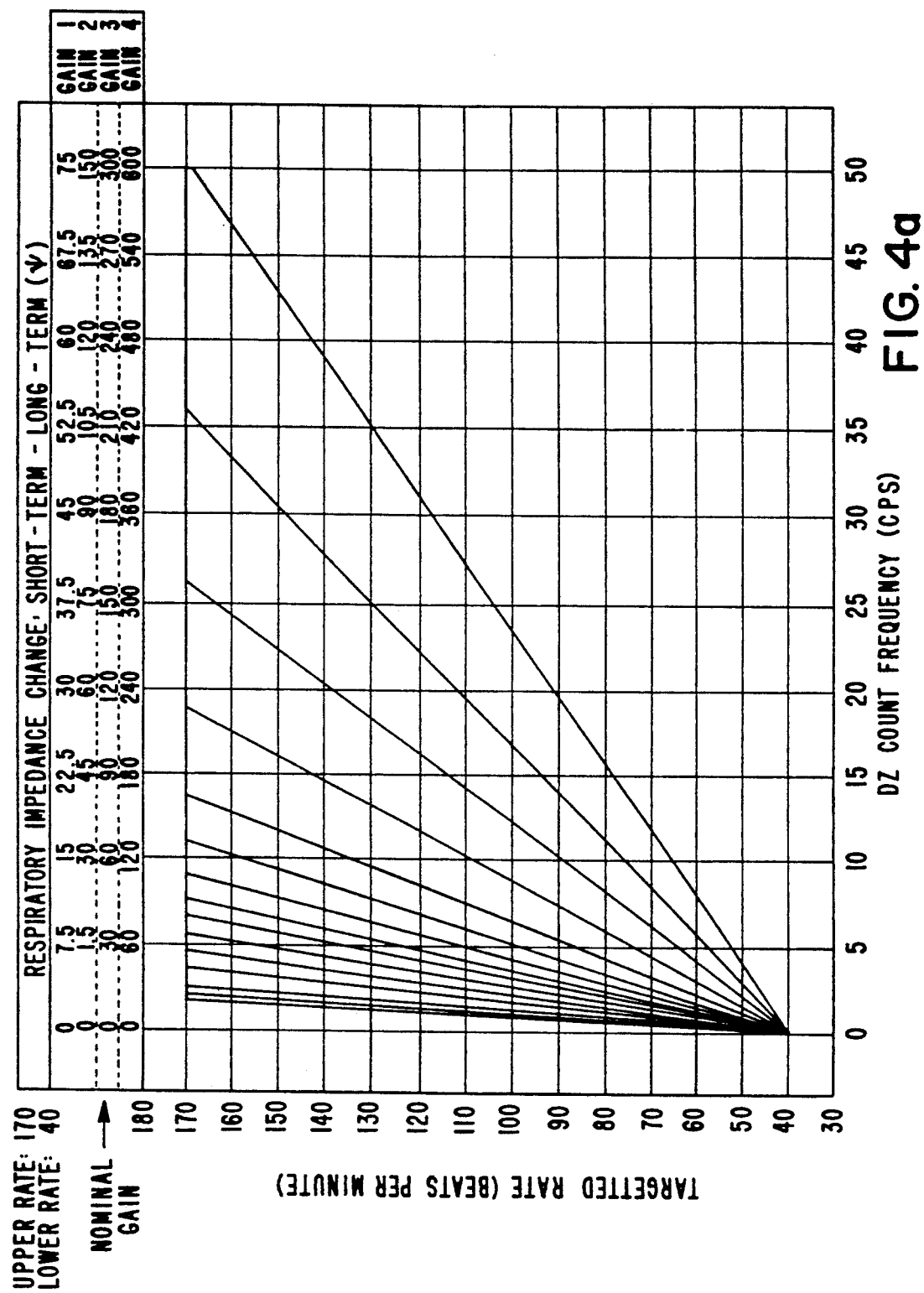
FIGS. 4a through 4d are graphs showing families of rate-response functions for the pacemakers of FIGS. 1 and 2.
Figure 4B:
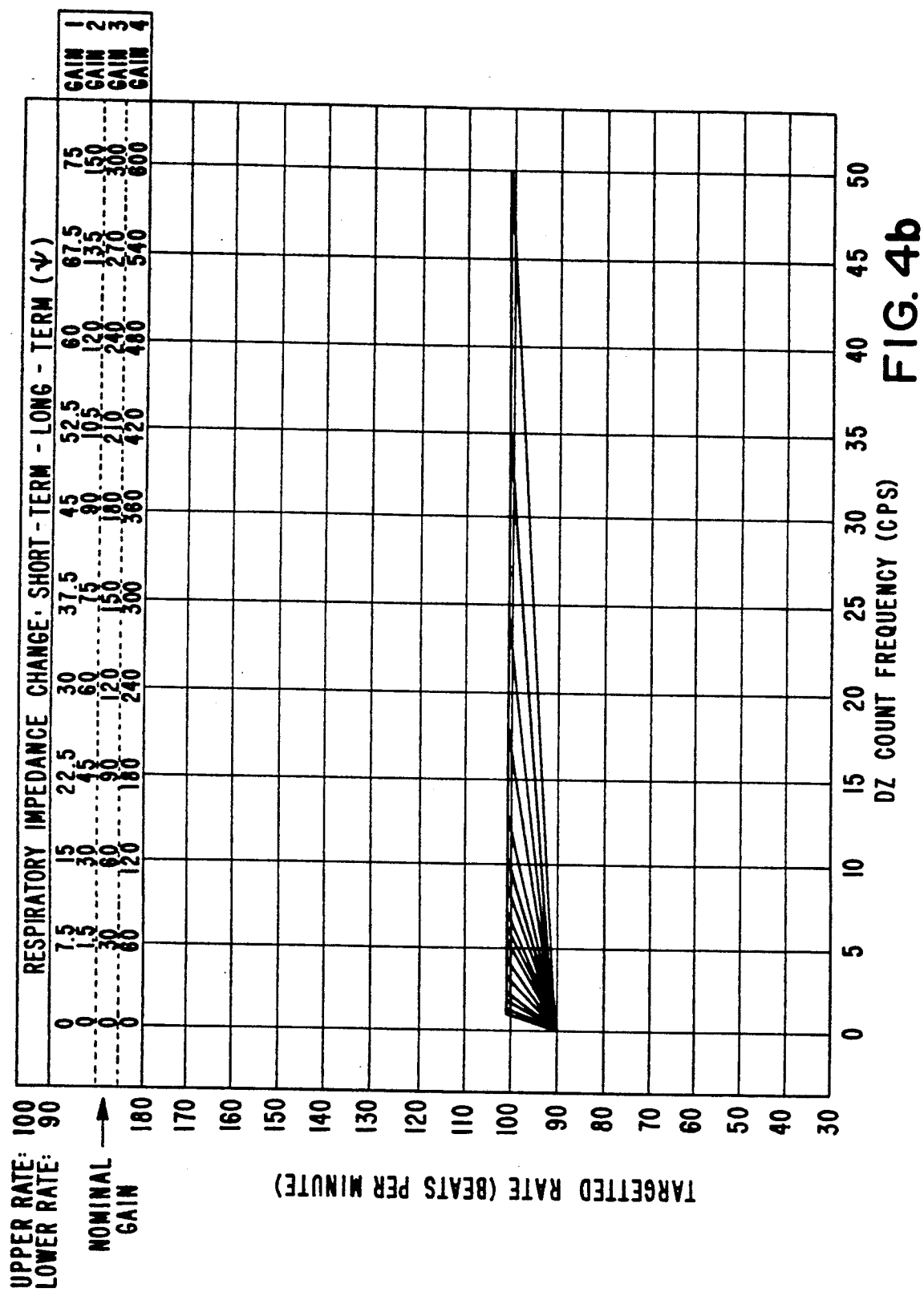
Figure 4C:
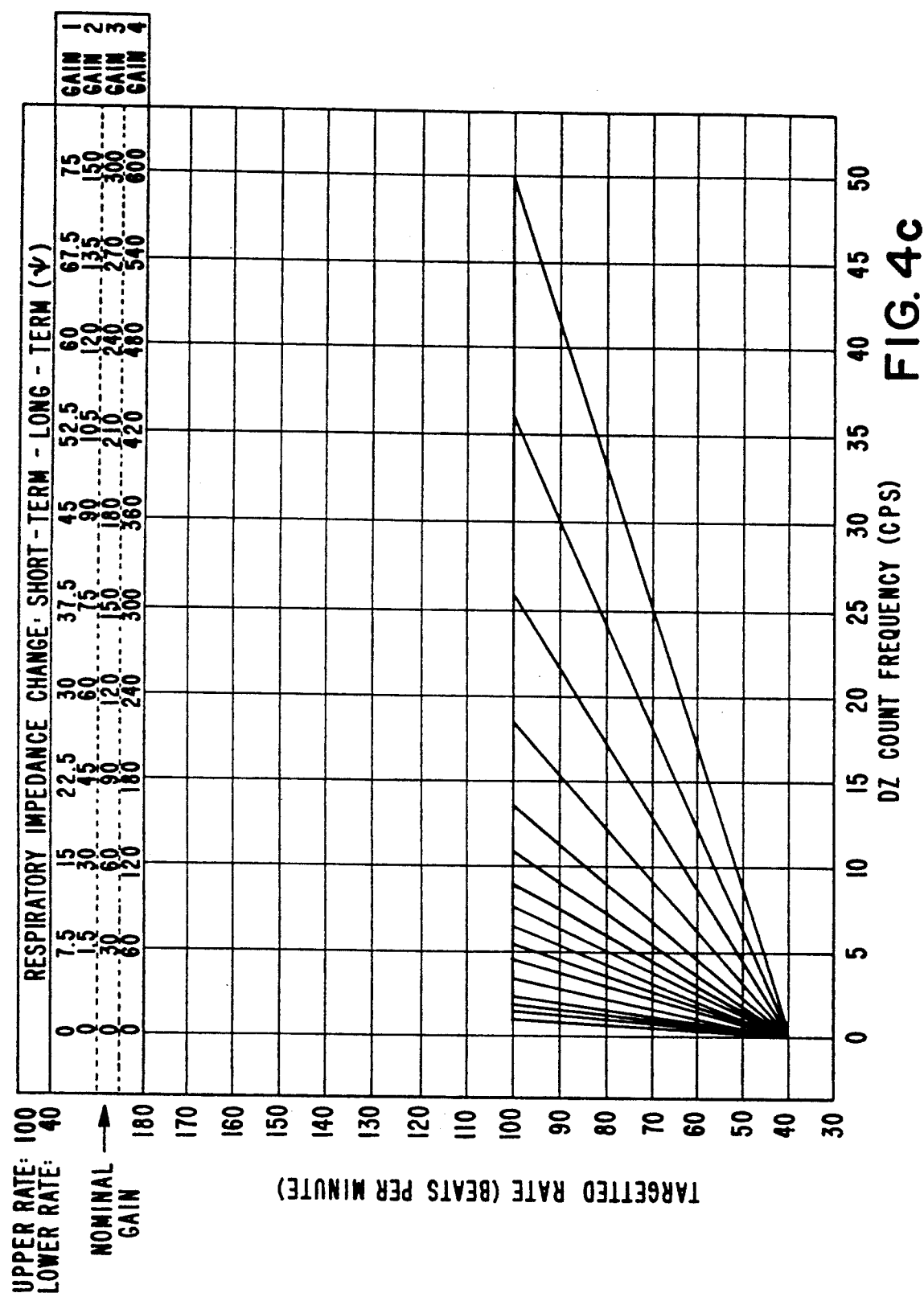
Figure 4D:
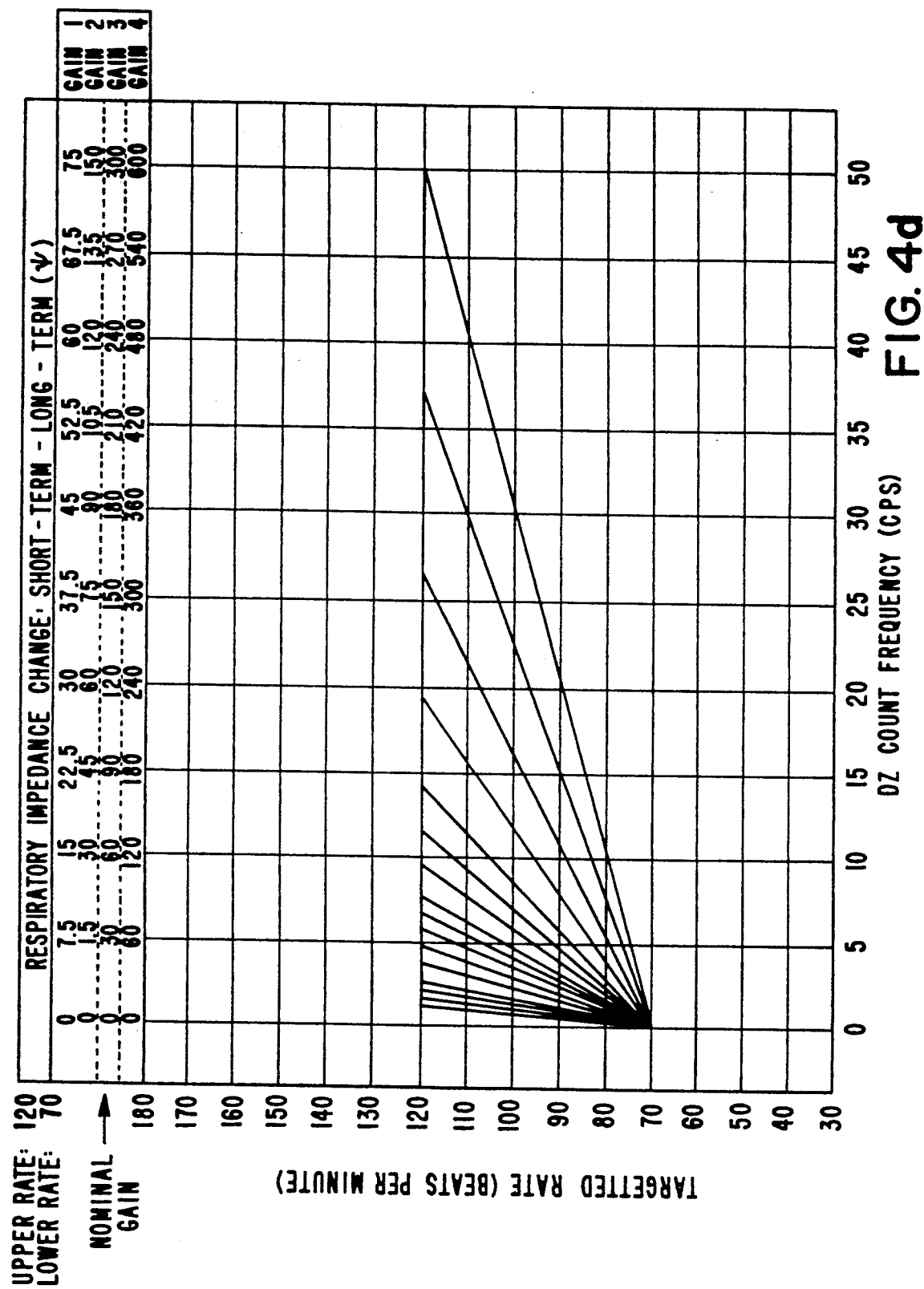

The graph of FIG. 4a, for example, shows the family of sixteen rate response curves resulting from setting the URL to 170 pulses per minutes (PPM) and the LRL to 40 PPM. In FIG. 4b, URL and LRL are 100 and 90 PPM, respectively. In FIG. 4c, URL and LRL are 100 and 40 PPM, respectively, and in FIG. 4d, URL and LRL are 120 and 70 PPM, respectively.

It should be noted with reference to FIGS. 4a through 4d that the computations of equations 1 through 13 above ensure that for any combination of programmed URL, programmed LRL, and programmed rate-response setting, the pacing rate remains variable along the full range between LRL and URL.

It is to be understood that FIG. 4a through 4d depict the families of rate-response curves for only some selected combination of URL and LRL; however, it is believed by the inventors that a person of ordinary skill in the art could reconstruct the family of rate-response curves for any allowable combination of URL and LRL through application of equations 1 through 13 above. In accordance with the presently disclosed embodiment of the invention, programming an LRL to a rate greater than or equal to URL is noted allowed.

Following calculation of a impedance-based target pacing period (TPP) in the manner described above, a rate smoothing function is calculated. As would be apparent to one of ordinary skill in the art, a rate smoothing function limits the rate of change in the range-responsive pacing period. The rate-smoothing function of pacemaker 10 in accordance with the presently disclosed embodiment of the invention is described in terms of variable NEWPP, which is defined as follows:

$$NEWPP = \begin{cases} CURPP + int\left\{ \frac{1}{2^{ATT}}(TPP - CURPP) \right\} : TPP < CURPP \\ CURPP + int\left\{ \frac{1}{2^{DEC}}(TPP - CURPP) \right\} : TPP \geq CURPP \end{cases} \quad (14)$$

where NEWPP is the "smoothed" target period, TPP is the impedance-based rate-responsive target pacing period as before; CURPP is the currently active rate-response period; ATT is a programmed rate smoothing attack constant; and DEC is a programmed rate smoothing decay constant. In accordance with the presently disclosed embodiment of the invention, ATT and DEC may take on programmed values of one through seven.

After NEWPP has been calculated, the current pacing period (CURPP) for the next pacing cycle is replaced with the NEWPP value. The new rate-responsive pacing rate is related to the CURPP value as follows:

$$RATE-RESPONSIVE\ RATE = \frac{60 \times f}{(CURPP+1) \times 258} \frac{beats}{min} \quad (15)$$

where f is the frequency of system clock 56, typically 32,768-Hz, and 258/f is the period of a "slow-clock" signal derived from the system clock. The slow-clock period is a multiple of the system clock period, and the slow-clock period is the basic unit in which various cardiac cycle timing intervals are measured in pacemaker 10.

Figure 5A:
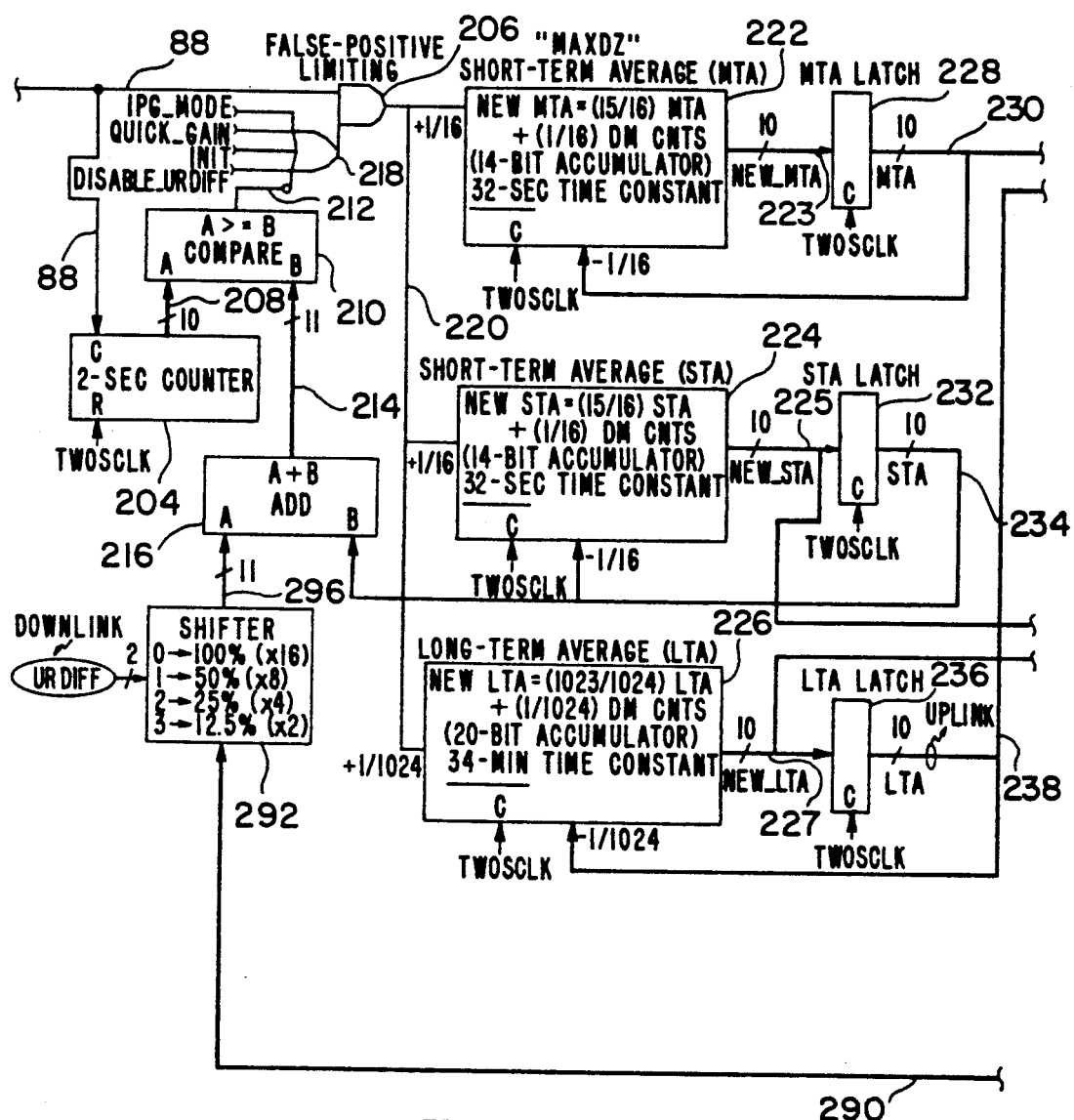
FIGS. 5a and 5b are block diagrams of the impedance circuit of the pacemaker of FIGS. 1 and 2.
Figure 5B:
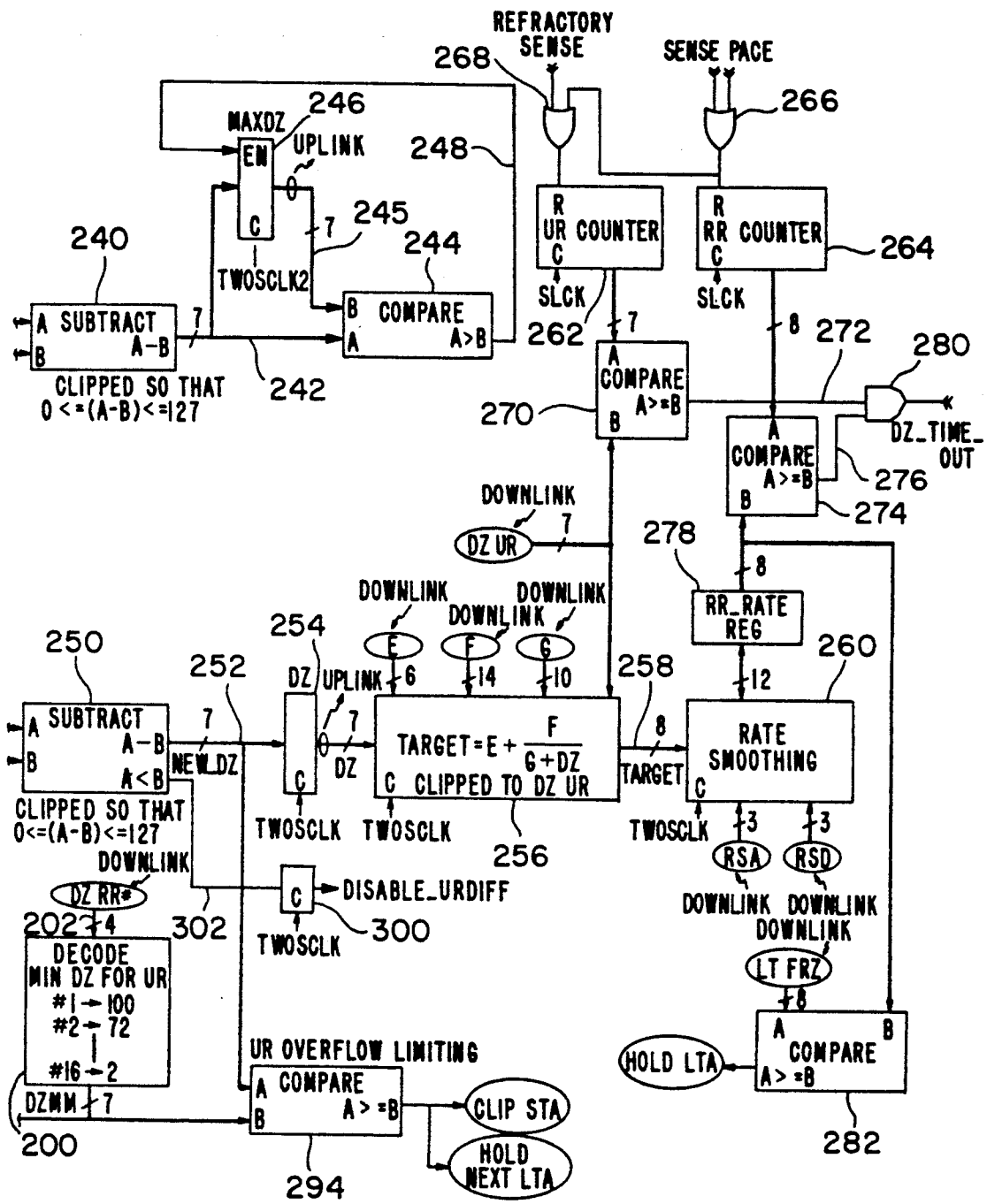

Turning now to FIG. 5, a block diagram of the circuitry within digital controller/timer circuit 50 which is responsible for computing the impedance-based rate-responsive pacing rate as described herein is shown. As can be seen from FIG. 5, several of the synchronous (i.e., clock-driven) components of the rate-responses circuitry, to be hereinafter described in greater detail, have applied thereto an input signal TWOSCLK. TWOSCLK is a two-second clock signal that is derived from system clock 56 in a conventional manner. It is to be understood that it is the same TWOSCLK signal that is being simultaneously applied to several components of the rate-responsive circuitry, even though the various TWOSCLK inputs in FIG. 5 are not shown as being interconnected.

In addition, several components of the circuitry of FIG. 5 are computational elements requiring externally supplied parameter values, such as are provided by a physician using an external programming device. In FIG. 5, programmable parameter values supplied to pacemaker 10 by means of a telemetry system such as described hereinabove are identified by their parameter name (e.g., UR_DIFF, E, F, G, etc...) within an ellipse, underneath a "DOWNLINK" label. For example, the impedance based-rate response setting (DZ RR#), which is a number between one and sixteen as previously described, is shown in FIG. 6 as being applied to DECODE circuit 200 via a four-conductor data path 202. For the sake of clarity, it is to be understood in FIG. 5 that the label "DOWNLINK" above a parameter name within an ellipse will serve as a representation that the parameter value identified in the ellipse is a value that is provided to pacemaker 10 by means of the telemetry system described hereinabove, including antenna 52 and RF Transmitter/Receiver 54 shown in FIG. 2. Similarly, it is to be understood that the label "UPLINK" associated with a given data path in FIG. 5 is intended to represent a data value which is available to telemetry circuit 54 to be transmitted to an external programmer, as previously described. For example, the UPLINK label on line 245 in FIG. 5 is to be taken as an indication that the MAXDZ value on line 245 is one of the values which can be transmitted to an external programmer upon interrogation of pacemaker 10.

In FIG. 5, the input signal DM is shown being applied by line 88 to the count (C) input of TWO-SECOND COUNTER 204, which also receives the TWOSCLK signal at is reset (R) input. DM, which is the serial bit-stream output of ΔZ Processor 100 previously described with reference to FIG. 2, is also applied to one input of AND gate 206.

The TWOSCLK signal applied to the reset input of TWO-SECOND COUNTER 204 causes the count value of TWO-SECOND COUNTER 204 to be reset to zero every two seconds. Immediately after reset, the count value in TWO-SECOND COUNTER 204 is incremented by one for every pulse of the DM signal on line 88. Since the number of pulses in the serial bit stream DM corresponds to the change in the input voltage to ΔZ Processor over the last 62.5 milliseconds, the count value in TWO-SECOND COUNTER 204 will vary accordingly.

The count value of TWO-SECOND COUNTER 204 is applied on 10-bit line 208 to a comparator 210. The signal on output line 212 from comparator 210 is asserted when ever the 10-bit value on line 208 becomes greater than or equal to the 11-bit value applied on line 214 from an adder 216. The signal on line 212 is applied to an inverting input of an OR gate 218, the output of which is applied to a second input of AND gate 206. Comparator 210, OR gate 218, and AND gate 206 implement the UR_DIFF clipping function described hereinabove. The output of OR gate 218 is typically a logical "1", going to a logical "0" value during initialization, when clipping of the input signal is required, as will be hereinafter described.

When the output of OR gate 218 is a logical "1", the serial bit stream DM on line 88 is propagated through AND gate and applied on line 220 to the inputs of a MAXDZ circuit 222, a SHORT-TERM AVERAGE (STA) circuit 224, and a LONG-TERM AVERAGE (LTA) circuit 226, MAXDZ circuit 222 produces a value NEW_MTA every two seconds, according to the recursive formula:

$$\text{NEW\_MTA} = \left(\frac{15}{16}\right)\text{MTA} + \left(\frac{1}{16}\right)\text{DM} \tag{16}$$

where MTA is the most recently calculated NEW_MTA value and DM is the sum of the number of pulses occurring in the DM bit stream in the last two-second interval. Every two seconds (as determined by TWOSCLK) MAXDZ circuit 222 produces a NEW_MTA value on 10-bit output line 223, and this value is latched in MTA LATCH 228 so that it is available on line 230 until a new NEW_MTA value is produced two seconds later.

Operation of SHORT-TERM AVERAGE (STA) circuit 224 is substantially identical to that of MAXDZ circuit 222. The DM serial bit stream is applied, via AND gate 206 and line 220 to an input of SHORT-TERM AVERAGE (STA) circuit 224. Every two seconds, SHORT-TERM AVERAGE (STA) circuit 224 produces a value NEW_STA on line 225, and this value is latched in STA LATCH 232 so that the NEW_STA value is available on line 234 for two seconds until a new NEW_STA value is calculated. The value NEW_STA is computed according to the following recursive formula:

$$\text{NEW\_STA} = \left(\frac{15}{16}\right)\text{STA} + \left(\frac{1}{16}\right)\text{DM} \tag{17}$$

where STA is the most recently computed NEW_STA value and DM is the sum of the number of pulses occurring in the DM bit stream in the last two-second interval.

Similarly, LONG-TERM AVERAGE (LTA) circuit 226 produces a value NEW_LTA on 10-bit output line 227 every two seconds, and this value is latched in LTA LATCH 236 so that it is available on line 238 for two seconds until a new NEW_LTA value is calculated. The NEW_LTA value is computed every two seconds according to the following recursive formula:

$$\text{NEW\_LTA} = \left(\frac{1023}{1024}\right)\text{LTA} + \left(\frac{1}{1024}\right)\text{DM} \tag{18}$$

where LTA is the most recently computed NEW_LTA value and DM is the sum of the number of pulses occurring in the DM bit stream in the last two-second interval.

Subtracting circuit 240 receives the value latched in MTA LATCH 228 at one input and the value latched in the LTA latch an another input. Subtracting circuit 240 performs the computation (MTA minus LTA). IF (MTA minus LTA) is less than zero, subtracting circuit 240 produces a zero binary value on 7-bit output line 242; if (MTA minus LTA) is greater than 127, subtracting circuit 240 produces a binary value of 127 on output line 242. If (MTA minus LTA) is between zero and 127, the actual result of the computation (MTA minus LTA) is produced on output line 242. As should be apparent to one of ordinary skill in the art, subtracting circuit performs the subtraction and clipping functions necessary to produce the variable UDZ previously discussed with reference to equation (7) above.

The UDZ value on line 242 is applied to inputs of a comparator 244 and a latch 246. Another input of comparator 244 has applied thereto, via line 245, the contents of latch 246. If comparator 244 determines that the UDZ value on line 242 is greater than the UDZ value currently stored in latch 246, comparator 244 asserts the signal on line 248, which is coupled to the enable input of latch 246. In this manner, whenever a UDZ value greater than any previously calculated UDZ value appears on line 242, it is stored in latch 246. Thus, latch 246 holds a value corresponding to the MAXDZ value previously discussed. It should be noted that line 245 is associated with an "UPLINK" label, indicating that the MAXDZ value may be transmitted by telemetry circuit 54 and antenna 52 to an external programmer performing an interrogation of pacemaker 10.

Subtracting circuit 250 receives the NEW_STA value on line 225 at one input and the NEW_LTA value on line 227 at another input. Subtracting circuit 250 performs the computation (NEW_STA minus NEW_LTA). If the result of this computation yields a result less than zero, subtracting circuit 250 produces a binary zero value on 7-bit output line 252. If the result of the computation (NEW_STA minus NEW_LTA) is greater than 127, subtracting circuit 250 produces a binary value 127 on output line 252. If the result of the computation (NEW_STA minus NEW_LTA) is between zero and 127, the actual result of the computation is produced on line 252. It should be apparent to one of ordinary skill in the art, therefore, that subtracting circuit 250 is performing the subtraction and clipping functions associated with the Limited Positive Difference (DZ) function previously described with reference to equation (6) above. The DZ output value from subtracting circuit 250 is conducted on line 252 to the input of DZ latch 254. Note that the output of DZ latch 254 is associated with an "UPLINK" label, indicating that DZ is one of the values which may be transmitted to an external programming device upon interrogation of pacemaker 10, as previously described.

The DZ value in latch 254 is applied to computational unit 256. Also applied to computational unit 256 are several programmable parameter values E, F, G, and DZ_UR. The programmable parameter values are provided to pacemaker 10 via telemetry, as previously described. Using these values, computational unit 256 performs the computation defined by equation (9) above, to determine a target pacing period (TPP) value. The TPP value produced by computation circuit 256 is limited to a minimum value of DZ_UR, which is one of the externally programmable values. That is, of the result of the computation performed by computational circuit 256 is less than DZ_UR, the value DZ_UR is substituted for the newly-computed TPP value. The TPP value is conducted on 8-bit line 258 to a rate-smoothing circuit 260.

Rate smoothing circuit 260 receives, in addition to the TPP value from computation circuit 256, downlink-telemetered values RSA and RSD, corresponding to externally programmed rate smoothing attack and decay parameters, respectively, previously discussed with reference to equation (14). Rate smoothing circuit performs the calculations defined in equations (14) and (15) above, and provides the resulting "smoothed" target period NEWPP to RR_RATE REGISTER 278. The NEWPP value stored in register 278 is provided to one input of comparator 274.

With continued reference to FIG. 5, an UR COUNTER 262 and an RR COUNTER 264 each receive a SLCK signal at their count inputs. SLCK is the "slow-clock" signal previously discussed with reference to equation (15); SLCK defines the basic unit of time in which various cardiac cycle timing intervals are measured. The output of an OR gate 266 is applied to the reset input of RR COUNTER 264, and the output of an OR gate 268 is applied to the reset input of UR COUNTER 268. The output of OR gate 266 is asserted whenever a sensed cardiac event occurs or a paced cardiac event occurs; thus, RR COUNTER 264 is reset whenever a sensed or paced cardiac event occurs. The output of OR gate 268 is asserted whenever the output of OR gate 266 is asserted, or whenever a cardiac event is sensed during a refractory period.

A comparator 270 receives the value held in the UR COUNTER at one of its inputs, and the downlink-telemetered DZ_UR value at its other input. If the UR COUNTER value is greater than or equal to the DZ_UR value, the output signal on line 272 is asserted. Comparator 274 receives, in addition to the NEWPP value from RR_RATE REGISTER 278 as previously described, the value held in the RR COUNTER 264. If comparator 274 determines that the RR COUNTER value is greater than or equal to the NEWPP "smoothed" target -acing period stored in RR_RATE REGISTER 278, the signal on output line 276 is asserted. The output signals from comparators 270 and 274 are applied to the inputs of an AND gate 280; when the signals lines 272 and 276 are simultaneously asserted, the output of AND gate 280 is asserted. The output of AND gate 280 is labelled DZ_TIME-OUT, and this signal is asserted when the impedance-based rate-responsive algorithm in accordance with the present invention indicatives that a pacing pulse should be delivered.

A comparator 282 in FIG. 5 receives at one input the NEWPP value stored in RR_RATE REGISTER 278, and receives the downloaded value LT FRZ at another input. The "Long-Term Freeze" function prevents the loss of rate-response during prolonged periods of exercise. When comparator 282 determined that the rate-responsive pacing rate (NEWPP) exceeds the midpoint of the programmed URL and LRL (i.e., LT FRZ),the signal HOLD LTA is asserted, temporarily inhibiting the average of the LTA.

The downlinked value DZ RR#, corresponding to the programmed rate response setting 1-16 for pacemaker 10, is received by decoder circuit 200. Decoder circuit 200 translates the programmed rate-response setting into a value representing the minimum DZ value ($DZ_{mm}$) required to reach the programmed upper rate limit at the selected rate-response setting. The translation of a DZ RR# value to a $DZ_{mm}$ value occurs according to the following table:

TABLE 2

| RATE RESPONSE SETTING | $DZ_{MM}$ |
|---|---|
| 1 | 100 |
| 2 | 72 |
| 3 | 51 |
| 4 | 37 |
| 5 | 27 |
| 6 | 22 |
| 7 | 18 |
| 8 | 15 |
| 9 | 13 |
| 10 | 11 |
| 11 | 9 |
| 12 | 7 |
| 13 | 5 |
| 14 | 4 |
| 15 | 3 |
| 16 | 2 |

The $DZ_{mm}$ value produced by decoder 200 is provided on 7-bit line 290 to a shifter 292, and to an input of a comparator 294. Shifter 292 shifts the $DZ_{mm}$ value 1, 2, 3, or 4 places to the left, depending upon the value UR_DIFF downlinked to pacemaker 10. The UR_DIFF value is used in "clipping" the DM input bit stream, as previously discussed with reference to equation (8). The shifted $DZ_{mm}$ value from shifter 292 is provided on 11-bit line 296 to an input of adder 216. Adder 216 adds the shifted $DZ_{mm}$ value to the current short-term average value from STA latch 232, and provides the result of this addition on line 214 to comparator 210. In the event that the value of TWO-SECOND COUNTER 204 does not exceed the value on line 214, the signal on line 212 stays at a logical "0" level. Since line 212 is applied to an inverting input of OR gate 218, the output of OR gate 218 stays at a logical "1" level whenever the signal on line 212 is at a logical "0" level. However, if the value of TWO-SECOND COUNTER 204 exceeds the value on line 2134, the output signal on line 212 is asserted. If no other input signals to OR gate 218 are asserted when line 212 is asserted, the output of OR gate 218 will go to a logical "0" level. When the output of OR gate 218 goes to a logical "0", the DM bit stream on line 88 is prevented from propagating through AND gate 206. As a result, the MAXDZ, STA, and LTA circuits 2222, 224, and 226 will not receive further DM bit pulses.

A comparator 294 receives the NEW_DZ value on line 252 at one input and the $DZ_{mm}$ value from decoder 200 at another input. If comparator 294 determines that the NEW_DZ value exceeds the $DZ_{mm}$ value, the output signals CLIP STA and HOLD NEXT LTA are asserted. The CLIP STA and HOLD NEXT signals assure that NEW_DZ (i.e., STA minus LTA) does not exceed $DZ_{mm}$ as described in the definition of LSTA hereinabove.

A single bit latch 300 receives an output signal on line 302 from subtracting circuit 250. If subtracting circuit 250 determines that the NEW_STA value from line 225 is greater than the NEW_LTA value on line 227, the output signal DISABLE_URDIFF from latch 300 is asserted. The signal DISABLE_URDIFF is one of the inputs to OR gate 218. When LSTA is less than LTA, DISABLE_URDIFF is asserted; this effectively disables the UR_DIFF clipping function, since the DM bit stream on line 88 cannot be prevented from propagating through AND gate 206 when DISABLE_UR-DIFF is asserted.

From the foregoing detailed description of a specific embodiment of the invention, it should be apparent that a rate-responsive pacemaker has been disclosed which is capable of automatically adjusting its pacing rate in response to changes in minute ventilation as measured by transthoracic impedance. While a particular embodiment of the present invention has been disclosed in detail, it is to be understood that this has been done for illustrative purposes only, and should not be taken as a limitation upon the scope of the present invention. It is contemplated by the inventors that various alterations, substitutions, and modifications to the disclosed embodiment may be made without departing from the spirit and scope of the invention as set forth in the appended claims.

For example, while the present disclosure relates to a single chamber pacemaker which would operate in the VVIR or AAIR mode, the invention is also equally applicable to dual chamber pacemakers of all types, including DDDR, DDIR, VDDR, and DVIR type pacemakers. In such embodiments, the interval to be varied may be the interval between atrial pacing pulses (DVIR and DDDR), the interval between ventricular pacing pulses (DDDR, DDIR, VDDR and DVIR), or the interval between a ventricular pulse and the next subsequent atrial pacing pulse (DDDR, DDIR, and DVIR). Moreover, the present invention is also believed to be useful in the context of multiple sensor pacemakers, in which the pacing rate is determined by a plurality of measured physical parameters. In such embodiments, the desired rate-responsive pacing interval for one sensor might be combined with the desired rate-responsive pacing interval for another sensor by weighted or unweighted averaging or by other methods.

RATE RESPONSE PROGRAMMING

The mapping of the DZ values to pacing rates as shown in FIGS. 4a through 4d is the impedance pacing rate response (RR). The following two interactive protocols can be used to optimize the RR for each patient:

Breathing Protocol

This protocol provides an approximation of the maximal respiration by observing the DZ values during 10 seconds of maximal breathing.

During the breathing protocol the patient is instructed to take maximal breaths during a 10 second countdown. The DZ counts that result are loaded into the upper bits of the USTA. At the completion of the 10 second countdown, the value is stored in the MAXDZ register and uplinked to the programmer. The programmer then uses a look-up table to recommend an appropriate value for DZ RR.

Exercise Protocol

This protocol provides optimization of the RR based on the MAXMV value produced during exercise.

At the beginning of the protocol, the previous MAXMV value is cleared. The patient is then instructed to perform an appropriate level exercise for a minimum of 2 minutes. During the protocol the MAXMV register records the peak DZ value. At the completion of the protocol the MAXMV value is uplinked and the programmer then uses a look-up table to recommend an optimal value for RR.

Thus, the present specification should be regarded as exemplary, rather than limiting in nature, with regard to the following claims.

What is claimed is:

1. A pacemaker, enclosed within a housing, comprising:
   a rate control circuit;
   a pulse generator adapted to be coupled to a patient's heart via a cardiac lead, and coupled to said rate control circuit, said pulse generator responsive to a triggering signal from said rate control circuit to generate a pacing pulse;
   said rate control circuit having means for producing triggering signals at a rate varying between predetermined upper and lower pacing rates;
   an activity sensor adapted to be coupled to said patient, producing an output signal indicative of patient activity;
   a $\Delta Z$ processor;
   an impedance circuit, adapted to be coupled to said heart via said cardiac lead and coupled to said $\Delta Z$ processor, said impedance circuit producing an impedance voltage waveform corresponding to changes in impedance in said heart;
   said $\Delta Z$ processor having sampling means for periodically sampling said impedance voltage waveform and further having means for producing a serial bit stream output signal in response to each said sample, the number of logical '1' bits (hereinafter referred to as 'counts') in said bit stream output signal corresponding to a change in said impedance voltage waveform;
   said rate control circuit receiving said bit stream output signal, and having counting means responsive to said bit stream output signal to count said counts occurring during a plurality of successive two-second intervals and having calculating means to calculate the following values:
   LTA (Long-Term Average): an average count, over a predetermined long-term interval, of said counts occurring in each two-second portion of said long-term interval;

LSTA (Limited Short-Term Average): an average count, over a predetermined short-term interval, of said counts occurring in each two-second portion of said short-term interval, where said rate control circuit constrains said LSTA value to a range determined by said predetermined upper and lower pacing rates;

DZ (Limited Positive Difference): a value representing a comparison of LSTA and LTA, defined as $$DZ = \begin{cases} 0: & LSTA < LTA \\ LSTA-LTA: & 0 \leq (LSTA-LTA) \leq DZ_{mm} \\ DZ_{mm}: & LSTA-LTA \geq DZ_{mm} \end{cases}$$

where $DZ_{mm}$ is a predefined upper limit on said DZ value and where said rate control circuit producing triggering pulses at a rate determined as a function of said DZ value.

2. A method of pacing a patient's heart, comprising the steps of:
   (a) producing an impedance waveform corresponding to changes in impedance in said heart;
   (b) delta-modulating said impedance waveform at a predetermined sampling rate to produce a serial output bit stream, such that for first and second successive samples, said output bit stream after said second sample comprises a sequence of N logical '1' bits (hereinafter referred to as 'counts'), where N reflects a change in said impedance waveform between said first and second samples;
   (c) computing an LTA (Long-Term Average) value representing an average count, over a predetermined long-term interval, of counts occurring during each two-second portions of said long-term interval;
   (d) computing an LSTA (Limited Short-Term Average) value representing an average count, over a predetermined short-term interval, of counts occurring in each two-second portion of said short term interval;
   (e) computing a DZ (Limited Positive Difference) value, representing a comparison of said LTA and said LSTA values, according to the formula $$DZ = \begin{cases} 0: & LSTA < LTA \\ LSTA-LTA: & 0 \leq (LSTA-LTA) \leq DZ_{mm} \\ DZ_{mm}: & LSTA-LTA \geq DZ_{mm} \end{cases}$$

where $DZ_{mm}$ is a predefined upper limit on said DZ value;
   (f) delivering cardiac pacing pulses to said heart at a rate determined as a function of said DZ value.

3. The method of claim 2 further comprising:
   (a) initializing said DZ (Limited Positive Difference) value to zero; and
   (b) initializing said pacing rate to a lower rate (LR).

4. The method of claim 3 further comprising:
   (a) energizing a delta-modulator for a predetermined loading period; and
   (b) loading output counts during said loading period from said delta-modulator into said LTA (Long-Term Average) value and into said LSTA (Limited Short-Term Average) value.

5. The method of claim 4 further comprising:
   (a) interrogating said LTA (Long-Term Average) value with a programmer; and
   (b) calculating an analog gain range value for said delta-modulator.

6. The method of claim 5 further comprising:
   (a) setting gain range value to a first gain range if said LTA value is less than or equal to a mid-range value of said delta-modulator counts; and
   (b) setting said gain range value to a second gain range if said LTA value is greater than a mid-range value of said delta-modulator counts, said second gain range being a greater gain range value than said first gain range.

7. The method of claim 6 further comprising:
adjusting said gain range value to a third gain range if said LTA value is greater than a mid-range value determined after said gain range value has been set at said second gain range, said third gain range being a greater range value than said second gain range.

8. The method of claim 7 further comprising:
adjusting said gain range value to a fourth gain range if said LTA value is greater than a mid-range value determined after said gain range value has been set at said third gain range, said fourth gain range being a greater range value than said third gain range.

9. A pacemaker, enclosed within a housing, comprising:
   a rate control circuit;
   a pulse generator adapted to be coupled to a patient's heart via a cardiac lead, and coupled to said rate control circuit, said pulse generator responsive to a triggering signal from said rate control circuit to generate a pacing pulse;
   said rate control circuit having means for producing triggering signals at a rate varying between predetermined upper and lower pacing rates;
   an activity sensor adapted to be coupled to said patient, producing an output signal indicative of patient activity;
   a $\Delta Z$ processor;
   an impedance circuit, adapted to be coupled to said heart via said cardiac lead and coupled to said $\Delta Z$ processor, said impedance circuit producing an impedance voltage waveform corresponding to impedance in said heart;
   said $\Delta Z$ processor having sampling means for periodically sampling said impedance voltage waveform and further having means for producing a serial bit stream output signal in response to each said sample, the number of logical '1' bits (hereinafter referred to as 'counts') in said bit stream output signal corresponding to a change in said impedance voltage waveform;
   said rate control circuit comprising a Long-Term average (LTA) circuit, having means for receiving said bit stream output signal and having computing means responsive to said bit stream output signal to compute a Long-Term Average (LTA) value corresponding to an average count, over a predetermined long-term interval, of said counts occurring in each two-second portion of said long-term interval;

said rate control circuit further comprising a Limited Short-Term Average (LSTA) circuit, having means for receiving said bit stream output signal and having computing means responsive to said bit stream output signal to compute a Limited Short-Term Average (LSTA) value corresponding to an average count, over a predetermined short-term interval, of said counts occurring in each two-second portion of said short-term interval, where said rate control circuit constrains said LSTA value to a range determined by said predetermined upper and lower pacing rates;

said rate control circuit further comprising a Limited Positive Difference (DZ) circuit, having means for receiving said LSTA and said LTA values and having computing means for computing a Limited Positive Difference (DZ), representing a comparison of said LTA and said LSTA values according to the formula $$DZ = \begin{cases} 0: & LSTA < LTA \\ LSTA - LTA: & 0 \leq (LSTA - LTA) \leq DZ_{mm} \\ DZ_{mm}: & LSTA - LTA \geq DZ_{mm} \end{cases}$$

where $DZ_{mm}$ is a predefined upper limit on said DZ value;

said rate control circuit producing triggering pulses at a rate determined as a function of said DZ value.

* * * * *